United States Patent [19]
DeGraw et al.

[11] Patent Number: 5,374,726
[45] Date of Patent: Dec. 20, 1994

[54] PROCESS FOR PREPARING 10-DEAZAAMINOPTERINS AND 5,10-AND 8,10-DIDEAZAAMINOPTERINS FROM PTEROIC DICARBOXYLIC ACID DIESTERS

[76] Inventors: Joseph I. DeGraw, 880 Hanover Ave., Sunnyvale, Calif. 94087; William T. Colwell, 1055 Del Norte, Menlo Park, Calif. 94025; James R. Piper, 3128 Dolly Ridge Dr., Birmingham, Ala. 35243

[21] Appl. No.: 28,431

[22] Filed: Mar. 9, 1993

Related U.S. Application Data

[63] Continuation-in-part of Ser. No. 845,407, Mar. 3, 1992, abandoned, and a continuation-in-part of Ser. No. 875,779, Apr. 29, 1992, abandoned, and a continuation-in-part of Ser. No. 938,105, Aug. 31, 1992, abandoned, and a continuation-in-part of Ser. No. 8,919, Jan. 26, 1993, abandoned.

[51] Int. Cl.$^5$ ............................................. C07D 475/08
[52] U.S. Cl. ..................................... 544/260; 544/279; 548/136; 548/201; 546/318; 546/326
[58] Field of Search ........................... 544/279, 260

[56] References Cited

U.S. PATENT DOCUMENTS 4,369,319  1/1983  De Graw et al. .................... 544/260
4,460,591  7/1984  De Graw et al. .................... 544/279
4,746,659  5/1988  De Graw et al. .................... 544/260

Primary Examiner—Donald R. Daus
Attorney, Agent, or Firm—Hana Dolezalova

[57] ABSTRACT

A process is provided for the preparation of 10-deazaaminopterins and 5,10- and 8,10-dideazaaminopterins starting from the corresponding homoterephthalic acid diester coupling the corresponding dicarboxylic acid diester having the formula:

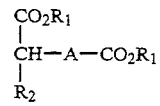

with the corresponding diaminopterin 6-methylene halide having the formula:

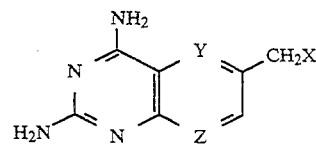

thereby forming a pteroic acid diester having the formula:

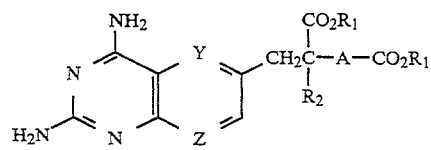

hydrolysing the two ester groups to form the corresponding carboxylic acid groups, and then monodecarboxylating the diacid, thereby removing the carboxylic acid group attached to the carbon alpha to the A group and forming a pteroic acid.

12 Claims, No Drawings

PROCESS FOR PREPARING 10-DEAZAAMINOPTERINS AND 5,10- AND 8,10-DIDEAZAAMINOPTERINS FROM PTEROIC DICARBOXYLIC ACID DIESTERS

This application is a continuation in part of Ser. No. 845,407, filed Mar. 3, 1992, Ser. No. 875,779 filed Apr. 29, 1992, Ser. No. 938,105 filed Aug. 31, 1992, all now abandoned and Ser. No. 80/008919 filed Jan. 26, 1993 abandoned.

U.S. Pat. No. 4,369,319 to DeGraw and Sirotnak, patented Jan. 19, 1983, discloses a new class of 10-deazaaminopterin compounds having the structure:

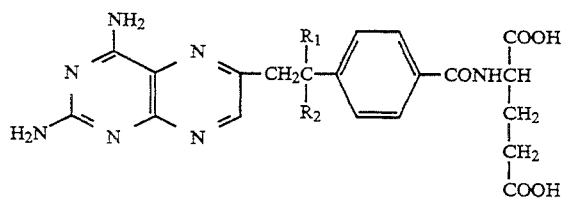

In the compound 10-deazaaminopterin, $R_1$ and $R_2$ are both hydrogen. In the alkyl derivatives of U.S. Pat. No. 4,369,319, either or both of $R_1$ and $R_2$ is alkyl having from one to about eight, preferably one or two carbon atoms. When only one of $R_1$ and $R_2$ is alkyl, the other is hydrogen.

Exemplary $R_1$ and $R_2$ alkyl include methyl, ethyl, propyl, isopropyl, butyl, isobutyl, secbutyl, tert-butyl, amyl, iso-amyl, sec-amyl, tert-amyl, hexyl, iso-hexyl, heptyl, iso-heptyl, octyl, iso-octyl, 2-ethyl hexyl and tert-octyl.

U.S. Pat. No. 4,369,319 discloses and its division, U.S. Pat. No. 4,433,147, patented Feb. 21, 1984, discloses and claims a synthesis for preparing 10-deazaaminopterin compounds including the following steps, starting from methoxymethyl acetylene (methyl propargyl ether):

Scheme I

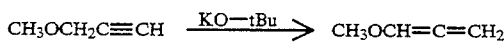

Stage 1

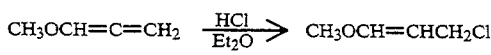

Stage 2

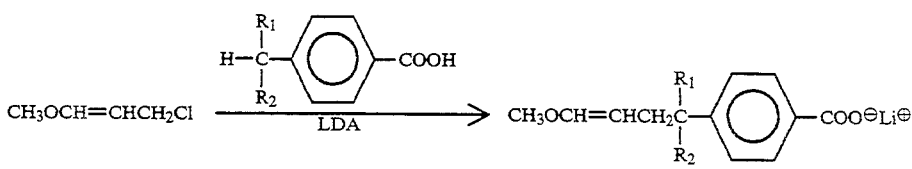

Stage 3

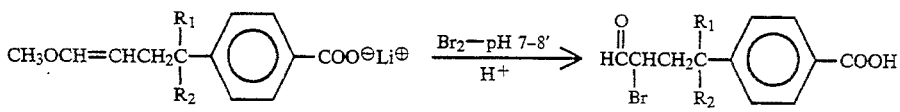

Stage 4

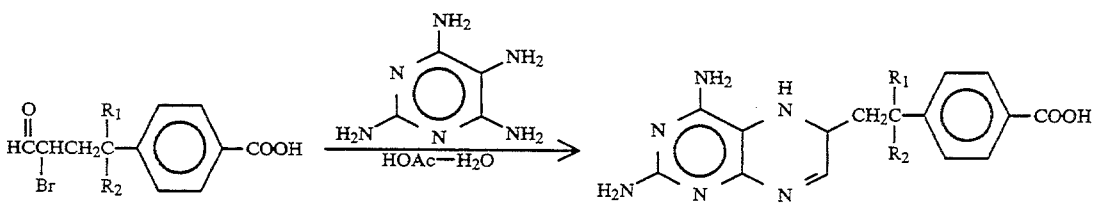

Stage 5

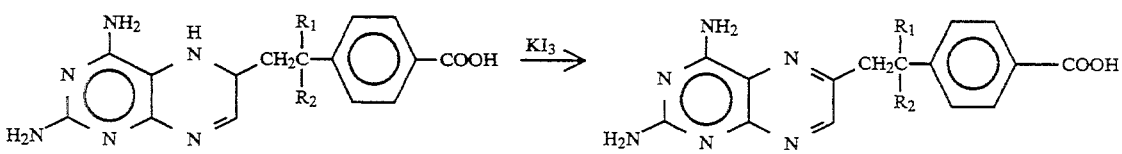

Stage 6

-continued
Scheme I
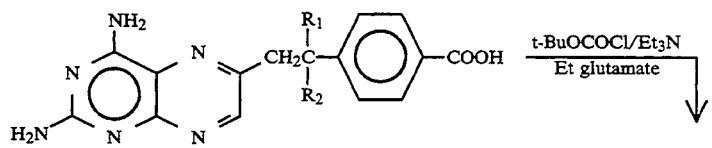
Stage 7
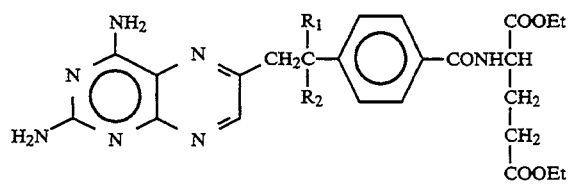
8
The preparation of 10-alkyl-8,10-dideazaaminopterin compounds as potential antitumor agents was revealed by DeGraw et al., J. Med. Chem.27,376(1984) and U.S. Pat. No. 4,460,591; Jul. 17, 1984. These compounds were prepared by the procedure shown in Scheme II below:
Scheme II
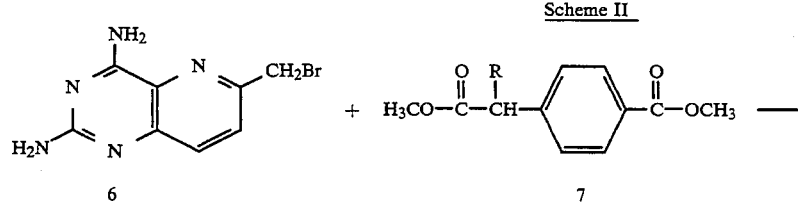
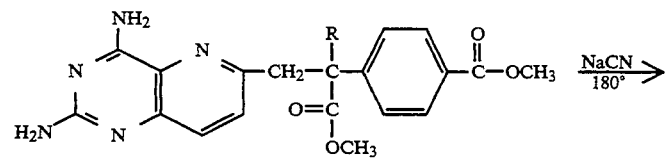
8
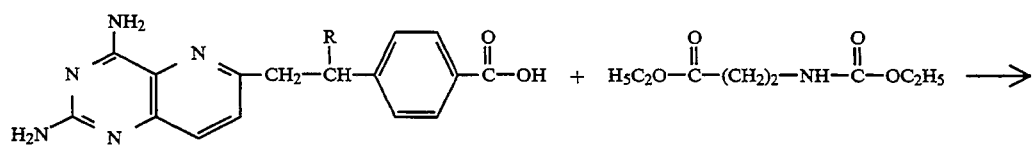
9     10
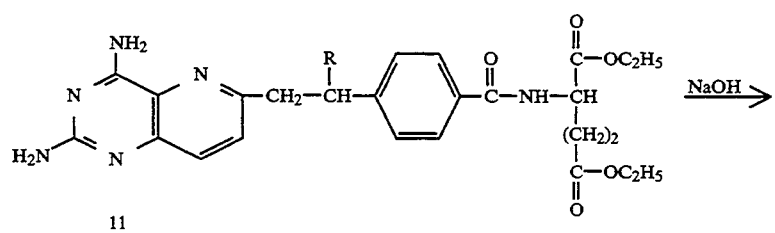
11
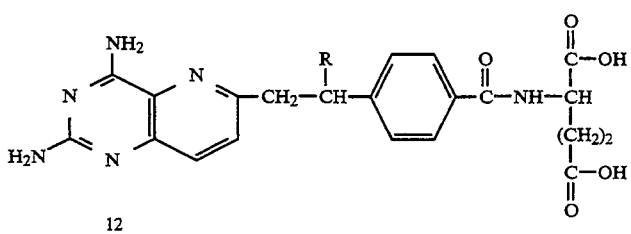
12

While this process was useful in the synthesis of certain 10-alkyl-8,10-dideazaaminopterin analogs, it was not considered suitable where the 10-substituent was alkenyl or alkynyl; or where a different pterin ring moiety was present (i.e., 2,4-diaminopteridine, 2,4-diamino-5-deazapteridine, etc.); or where the benzoate moiety was replaced by heteroaryl groups. The difficulty with the above procedure is the general lack of reproducibility and tendency to give poor yields of impure products in the cyanide-mediated decarbomethoxylation step. Temperatures of 180° C. or greater were often required to effect this key step.

The improved process for preparation of the key 2,4-diamino pteroic acid intermediates as described in this patent avoids the use of sodium cyanide and the high temperature process required to achieve the decarbomethoxylation. In this improved process, the 10-carboxy diester intermediate is saponified at room temperature with aqueous alkali to afford the 10-carboxy-2,4-diaminopteroic acids in high yield. Subsequent thermal decarboxylation is smoothly and rapidly carried out in dimethyl sufoxide (or other suitable solvent) at temperatures generally in the range of 100°–140° C. and occasionally from 25° to 100° C., again in high yield. Of course, temperatures above 140° C. can be used in some cases, especially to increase the rate of decarboxylation.

In the *Journal of Medicinal Chemistry* 17552(1974) DeGraw, Kisliuk, Gaumont, Baugh, and Nair reported on the synthesis and antifolate activity of 10-deazaaminopterin. The antimicrobial and antitumor activities of the powerful dihydrofolic reductase inhibitors aminopterin and its N-10 methyl derivate, methotrexate, are well known, and numerous analogues have been made to further improve the potency, cell penetration and toxicity properties of these compounds. As part of a continuing program to investigate structure-activity relationships in folic acid analogues, DeGraw et al. were interested in the effects of replacement of the nitrogen atom in the side chain of aminopterin, and reported on the synthesis and biological activity of 10-deazaaminopterin in this paper. Continuing work with 10-deazaaminopterin and its 10-alkyl derivatives has now led to the discovery of their antileukemic activity, and to their efficacy in treating various ascites tumor systems.

In accordance with U.S. Pat. No. 4,369,319, it has been determined that leukemia, as well as other malignancies, including ascitic tumors, can be ameliorated in warm-blooded lower animals by the administration of 10-deazaaminopterin, a nontrivial analogue of methotrexate, the current drug of choice for the treatment of leukemia in the clinic, as well as 10-alkyl derivatives of 10-deazaaminopterin, and it is expected that these compounds will have a similar effect in humans.

Rheumatoid arthritis is an inflammation of the joints arising from infectious, metabolic, or constitutional causes, usually of known origin. It can result in serious restriction of movement, and even invalidism. Since rheumatoid arthritis is a common disease that affects 2–3 million people in the United States alone, is poses a serious treatment problem. A substantial proportion of affected individuals will develop erosive joint disease and require surgical joint replacement despite therapies including disease-modifying antirheumatic drugs such as gold complexes, penicillamine, antimalarials, and methotrexate. In some patients with intractable RA, immunosuppressive agents including azathioprine, methoxtrexate, cyclophosphamide, and combinations of these drugs have been proven beneficial. However, the potential side effects of some of these drugs, including bone marrow toxicity and neoplasia, have limited their frequency of use and the dose that is given.

The disease is one of a number of forms of proliferative disease, and the development of drugs for amelioration or curing the disease has occupied the attention of research organizations for many years, and until most recently without appreciable success.

The antifolic acid drug, methotrexate (MTX), has been used as an antitumor agent since 1955. Its cytotoxic action in tumors is related to its ability to inhibit (essentially irreversibly) the key enzyme, dihydrofolate reductase, required for biosynthesis of tetrahydrofolic acid. Tetrahydrofolate is a vital component in one-carbon metabolism in cells, being required for biosynthesis of purine and pyrimidine nucleosides of the DNA and RNa. The drug is a powerful cytotoxic agent whose principal toxicities occur with liver, kidney, and mucosal tissue. Liver toxicity is the paramount concern for use in chronic therapy in a disease such as arthritis.

The ability of MTX to affect the inflammatory conditions of rheumatoid arthritis may be linked to its cytotoxic behavior. This may be in the nature of immune suppression and could involve attack on inflammatory phagocytic cells such as macrophages or neutrophils and T-helper cells in the synovial region. Very few MTX analogs have been evaluated against arthritis in animals, and there is no clear indication whether the antiarthritic properties are directly proportional to cytotoxicity. Galivan and co-workers (J. Galivan, M. Rehder, S. Kerwar, *Chem. Biol,*. Pteridines, 1986, DeGruyter, Berlin, p. 847) showed that adjuvant arthritis and streptoccocal cell wall arthritis in rats responded to doses of MTX relative to those used in man for treatment of RA. They also found that timing of dosage was most important for reduction of inflammation. Both MTX and aminopterin were found to inhibit inflammation, but other antifolate compounds that did not posses a 2,4-diaminopyrimidine unit or a benzoylglutamate side chain were ineffective.

Ser. No. 845,407, filed Mar. 3, 1992 provides 10-alkyl, 10-alkenyl, and 10-alkynyl 10-deazaaminopterin compounds having the structure:

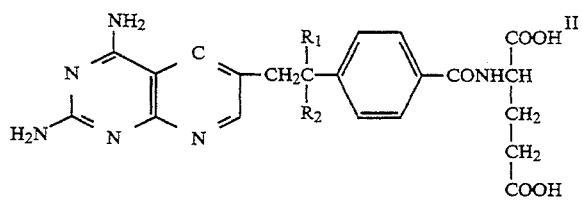

$R_1$ and $R_2$ are selected from the group consisting of hydrogen and alkyl, alkenyl, and alkynyl having from one to about eight, preferably from three to five, carbon atoms.

The invention also provides a process of treating leukemia and ascitic tumors which comprises administering to a warm-blooded animal having an abnormal proportion of leukocytes or other evidence of the malignancy, a therapeutic nontoxic amount of a 10-alkenyl or 10-alkynyl 10-deazaaminopterin compound as defined above, as such or in the form of a pharmaceutically acceptable salt thereof. These salts are formed with one or more free $NH_2$ groups and/or $COOH$ groups of the 10-deazaaminopterin compound.

The invention further provides a process of treating arthritis and other proliferative diseases, which comprises administering to a warm-blooded animal having an inflammation of the joints or other evidence of the disease, a therapeutic and relatively nontoxic amount of a 10-alkenyl or 10-alkynyl 10-deazaaminopterin compound as defined above, as such or in the form of a pharmaceutically acceptable salt thereof, as defined above.

The process disclosed in Ser. No. 845,407 for preparing 10-alkenyl and 10-alknyl 10-deazaaminopterin compounds is a synthesis including the following steps (Scheme A,B):

Ser. No. 875,779, filed Apr. 29, 1992 of which this application is a continuation-in-part, provides 5-alkyl, 5-alkenyl, and 5-alkynyl-5-deazaaminopterin and 5,10-dideazaaminopterin compounds having the structure:

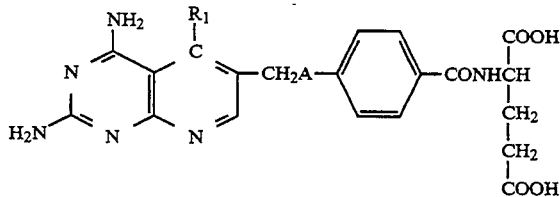

A is selected from the group consisting of N-$R_2$ and CH$R_2$.

$R_1$ and $R_2$ are hydrogen, or alkyl, alkenyl or alkynyl having from one to about eight carbon atoms, as above, in Formula II.

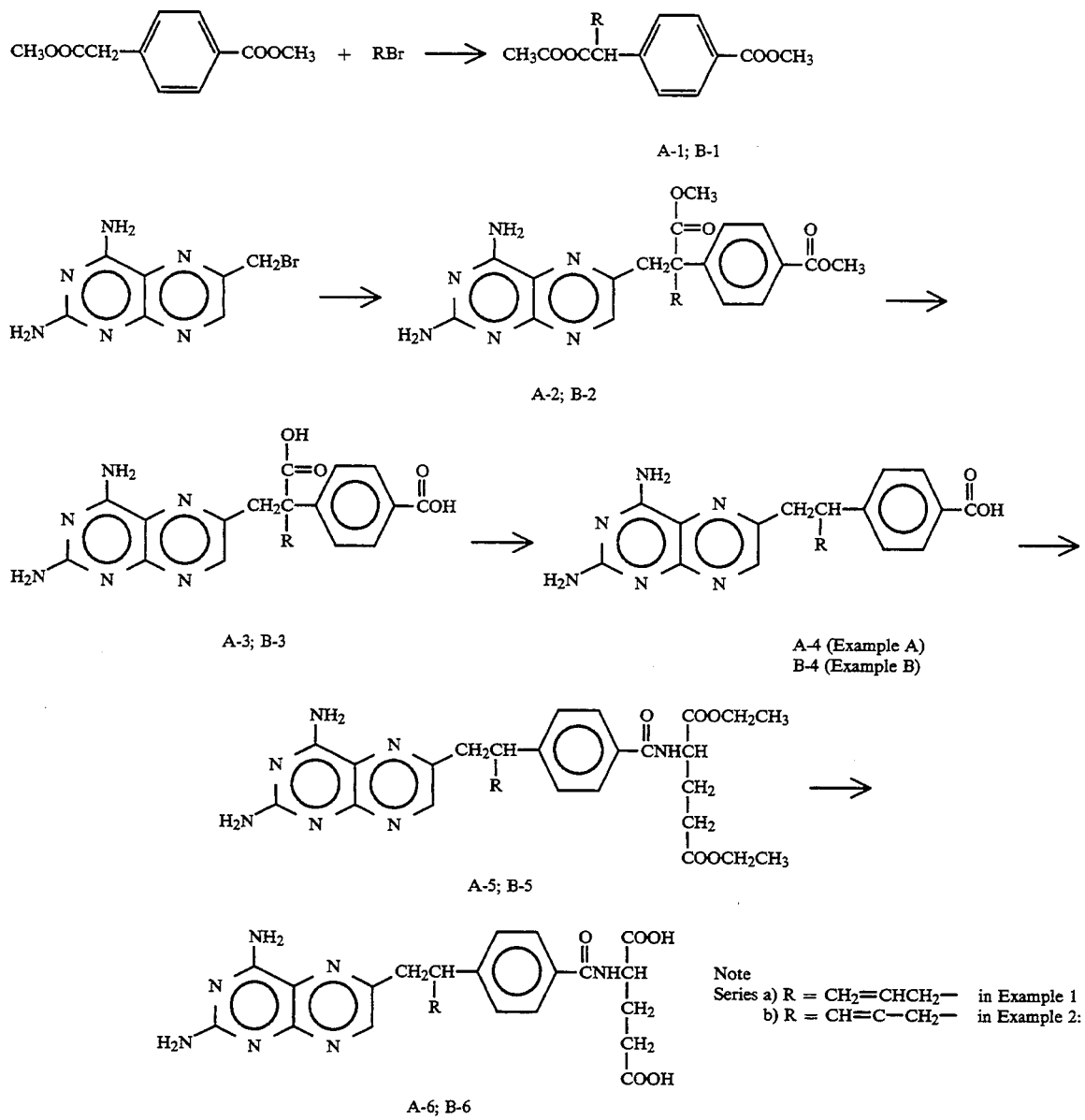

Note
Series a) R = CH$_2$=CHCH$_2$—  in Example 1
    b) R = CH≡C—CH$_2$—  in Example 2:

Ser. No. 875,779 also provides a process for treating arthritis and other proliferative diseases which comprises administering to a warm-blooded animal having an inflammation of the joints or other evidence of the disease, a therapeutic and relatively nontoxic amount of a 5-alkyl, 5-alkenyl, or 5-alkynyl-5-deazaaminopterin or 5,10-dideazaaminopterin compound as defined above, as such or in the form of a pharmaceutically acceptable salt thereof, as defined above.

The synthesis of the compounds of the above formula, A is N-R$_2$, is adapted from that reported by Piper et al. in *J. Med. Chem.* (1986)29, 1080–1087.

The synthesis of the compounds of the above formula

Scheme III

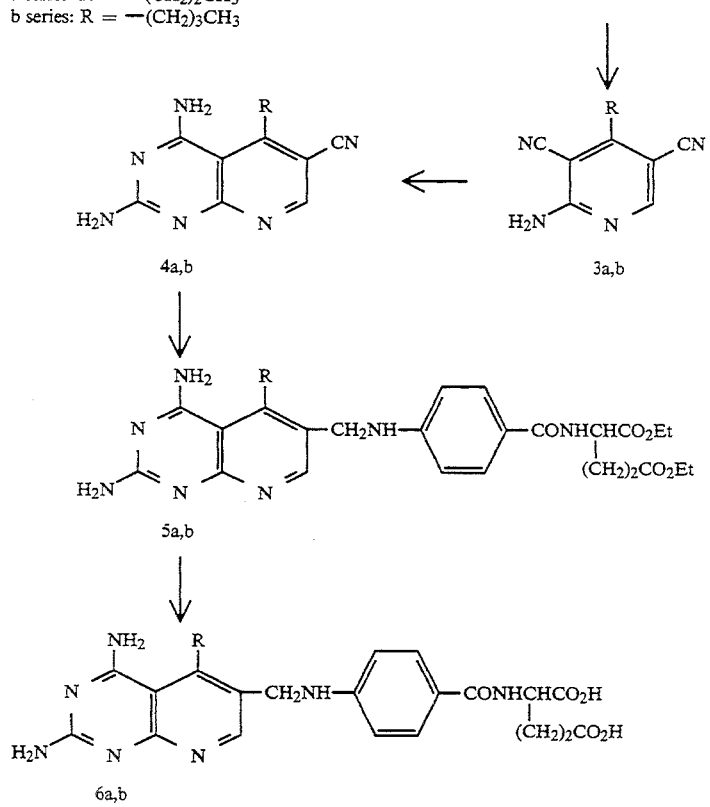

where A is CHR$_2$ is described in Ser. No. 875,779 and is outlined in Scheme C:

Scheme C

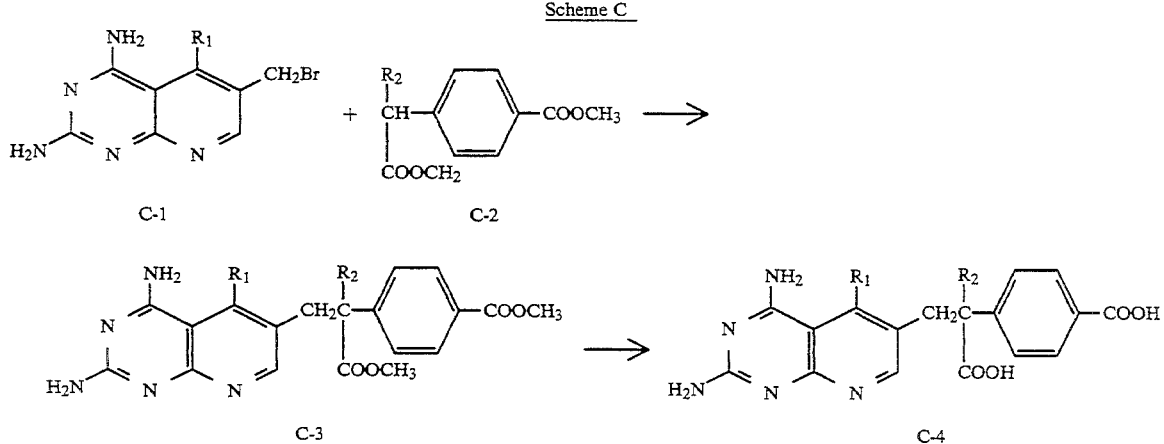

-continued
Scheme C

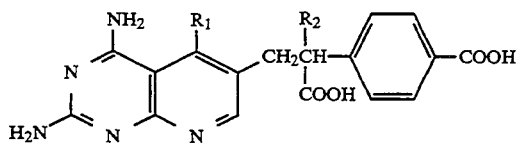

C-5 (R$_1$ = R$_2$ = H, Example C)

R$_1$ = H, alkyl
R$_2$ = H, alkyl, alkenyl, alkynyl

Ser. No. 938,105 filed Aug. 31, 1992, provides heteroaroyl-10-deazaaminopterin compounds having the structure:

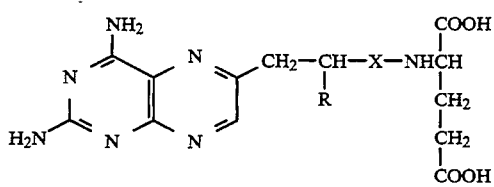

X is selected from this group consisting of

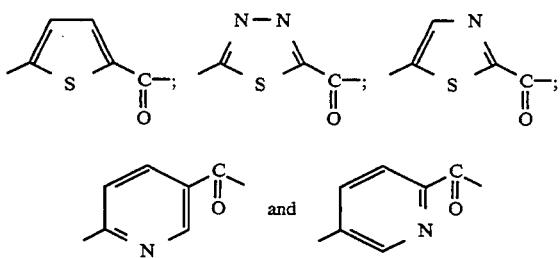

R is selected from the group consisting of hydrogen and alkyl, alkenyl, and alkynyl having from one to about eight, preferably from three to five, carbon atoms.

Exemplary R alkyl including methyl, ethyl, propyl, iso-propyl, butyl, isobutyl, sec-butyl, tert-butyl, amyl, iso-amyl, sec-amyl, tert-amyl, hexyl, iso-hexyl, heptyl, iso-heptyl, octyl, iso-octyl, 2-ethyl hexyl and tert-octyl.

Exemplary R alkenyl including allyl, 1-propenyl, crotyl (2-butenyl), 2-pentenyl, 4-pentenyl, 2-hexenyl, 5-hexenyl, 3-isopropenyl, 3-isobutenyl, and 4-octenyl.

Exemplary R alkynyl include propargyl, 2-butynyl, 3-butynyl, 4-pentynyl, 5-hexynyl, and 7-octynyl.

Ser. No. 938,105 also provides a process of treating arthritis and other proliferative diseases, which comprises administering to a warm-blooded animal having an inflammation of the joints or other evidence of the disease, a therapeutic nontoxic amount of a heteroaroyl-10-deazaaminopterin compound as defined above, as such or in the form of a pharmaceutically acceptable salt thereof. These salts are formed with one or more free NH$_2$ groups and/or COOH groups of heteroaroyl-10-deazaaminopterin compound.

These compounds are believed to be novel, and in addition are effective in the treatment of arthritis.

One subclass of thienyl compounds and thienyl analogues within Ser. No. 938,105 accordingly is defined by the formula:

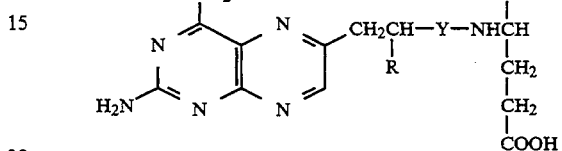

wherein
Y is selected from the group consisting of

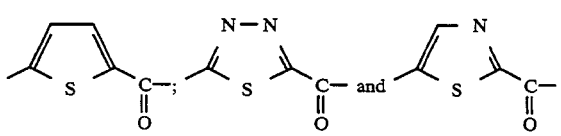

R is selected from the group consisting of hydrogen and alkyl, alkenyl, and alkynyl having from three to about eight, preferably from three to five, carbon atoms.

Another subclass of pyridyl compounds within Ser. No. 938,105 accordingly is defined by the formula:

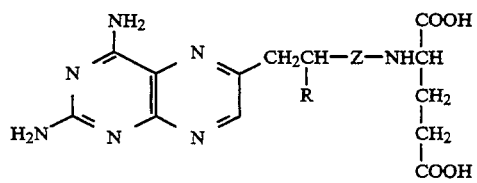

wherein
Z is selected from the group consisting of

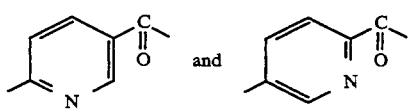

R is selected from the group consisting of hydrogen and alkyl, alkenyl, and alkynyl having from three to about eight, preferably from three to five, carbon atoms.

Ser. No. 8919 filed Jan. 26, 1993 provides heteroaroyl-5-deazaaminoperin and 5,10-dideazaaminopterin compounds having the structure:

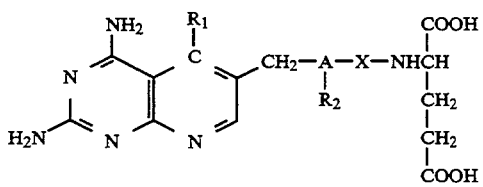

wherein

A is CH or N;
X is selected from the group consisting of

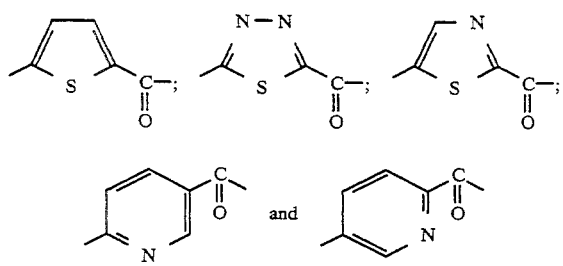

R₁ is selected from the group consisting of hydrogen and alkyl having from one to about eight, preferably from one to three, carbon atoms.

R₂ is selected from the group consisting of hydrogen and alkyl, alkenyl, and alkynyl having from one to about eight, preferably from one to three, carbon atoms.

Exemplary R₁ and R₂ alkyl include methyl, ethyl, propyl, iso-propyl, butyl, isobutyl, sec-butyl, tert-butyl, amyl, iso-amyl, sec-amyl, tert-amyl, hexyl, iso-hexyl, heptyl, iso-heptyl, octyl, iso-octyl, 2-ethyl hexyl and tert-octyl.

Exemplary R₂ alkenyl include allyl, 1-propenyl, crotyl (2-butenyl), 2-pentenyl, 4-pentenyl, 2-hexenyl, 5-hexenyl, 3-isopropenyl, 3-isobutenyl, and 4-octenyl.

Exemplary R₂ alkynyl include propargyl, 2-butynyl, 3-butynyl, 4-pentynyl, 5-hexynyl, and 7-octynyl.

The invention also provides a process of treating arthritis and other proliferative diseases, which comprises administering to a warm-blooded animal having an inflammation of the joints or other evidence of the disease, a therapeutic nontoxic amount of a heteroaroyl-5-deazaaminopterin or 5,10-dideazaaminopterin compound as defined above, as such or in the form of a pharmaceutically acceptable salt thereof. These salts are formed with one or more free $NH_2$ groups and/or COOH groups of the heteroaroyl-5-deazaaminopterin, or 5,10-dideazaaminopterin compound.

These compounds are believed to be novel, and in addition are effective in the treatment of arthritis.

One subclass of thienyl compounds and thienyl analogues within the invention accordingly is defined by the formula:

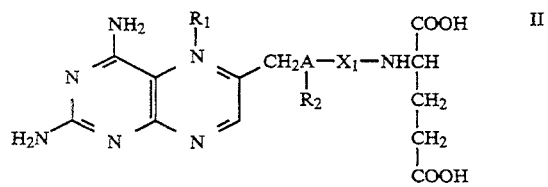

wherein
A is CH or N; X₁ is selected from the group consisting of

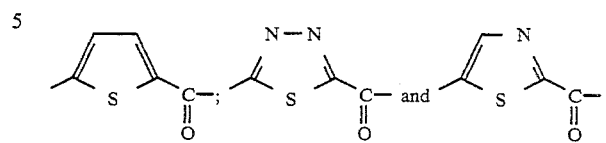

R₁ is selected from the group consisting of hydrogen and alkyl having from one to about eight, preferably from one to three, carbon atoms.

R₂ is selected from the group consisting of hydrogen and alkyl, alkenyl, and alkynyl having from three to about eight, preferable from one to three, carbon atoms.

Another subclass of pyridyl compounds within the invention accordingly is defined by the formula:

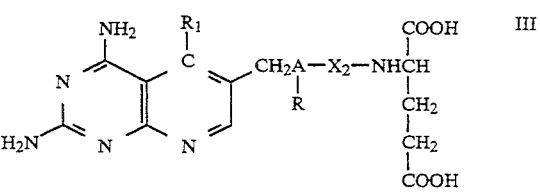

wherein
A is CH or N;
X₂ is selected from the group consisting

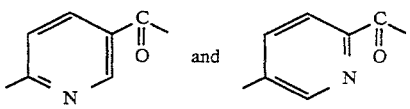

R₁ is selected from the group consisting of hydrogen and alkyl having from one to about eight, preferably from one to three, carbon atoms.

The synthesis of compound of Formulae I, II, and III wherein A is N and X is any of the heterocyclic rings set out for these formulae can be carried out by Scheme IV which follows.

The synthesis of compounds of Formulae I, II, and III wherein A is CH can be carried out by either of Schemes D and E which follow. Schemes D and E are novel and are believed to be patentable, and are the subject of copending patent applications.

Scheme IV

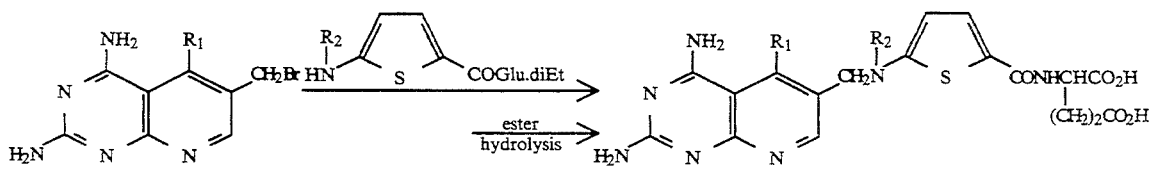

R₁ = H, alkyl
R₂ = H, aklyl

Scheme D
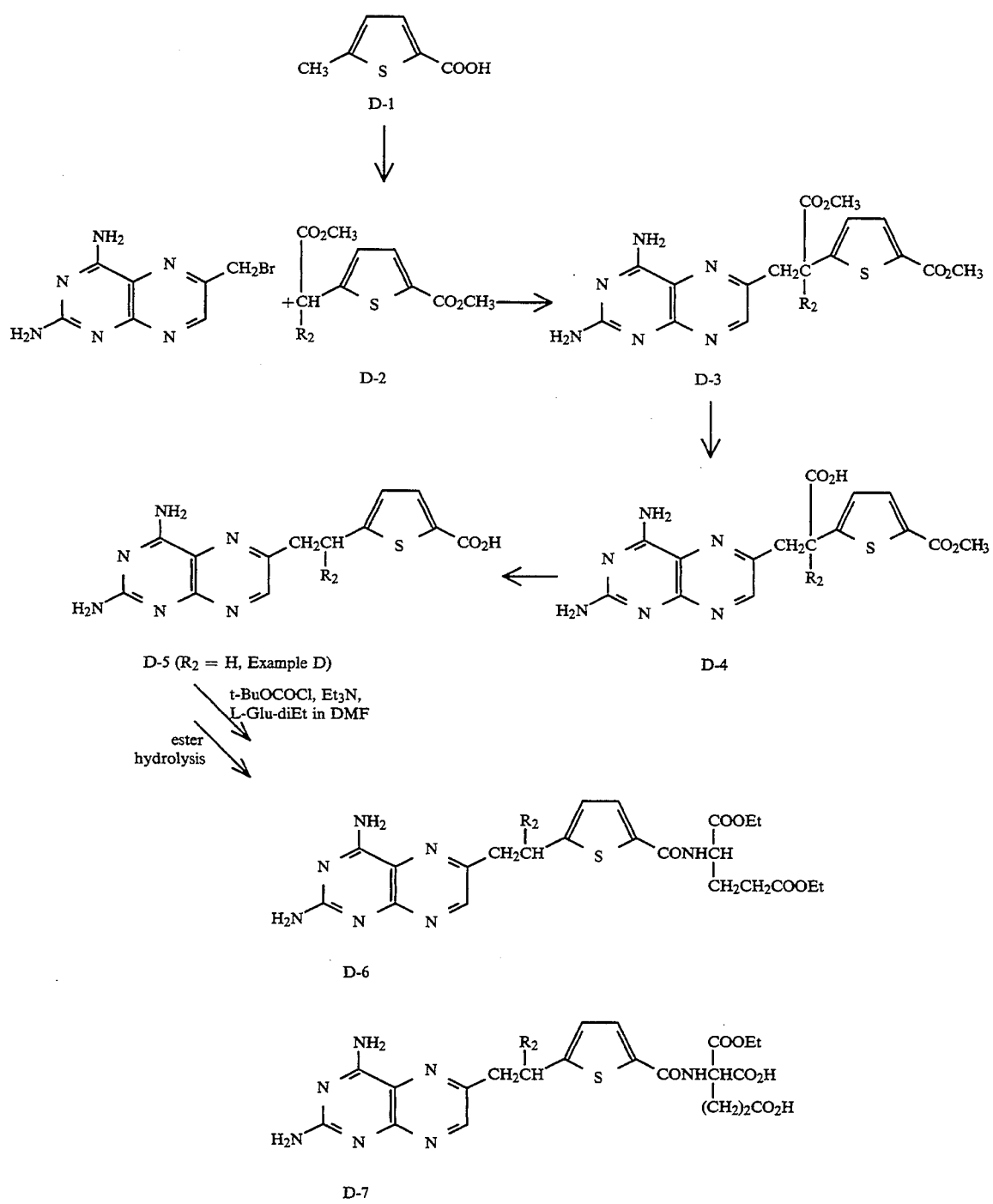
Scheme E
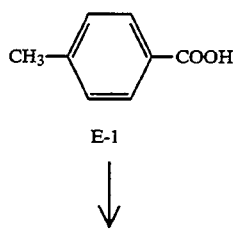

Scheme E
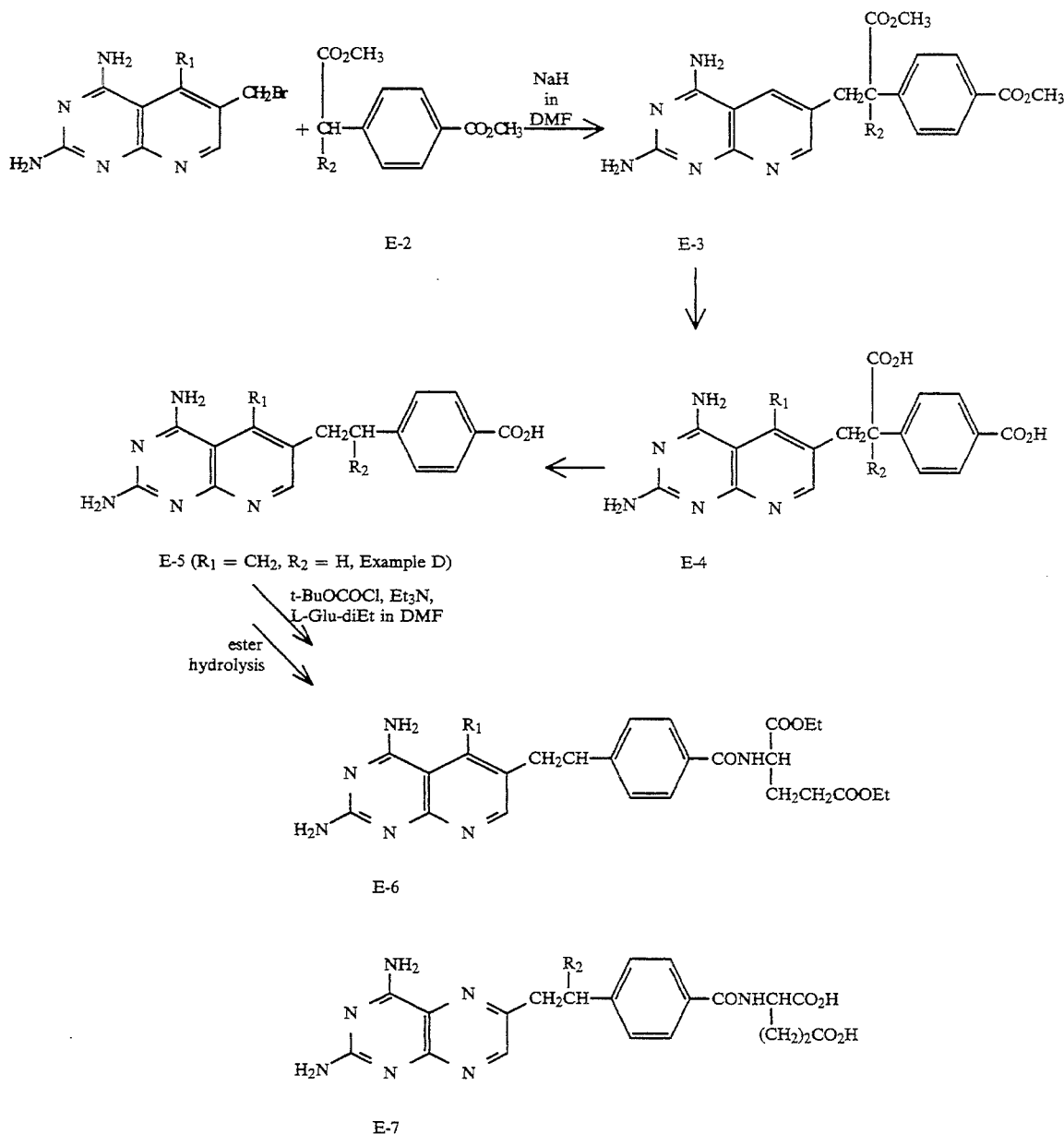
Synthesis of 8,10-dideazaaminopterin compounds has also been accomplished by the process of the present application as outlined in Scheme F.
Scheme F
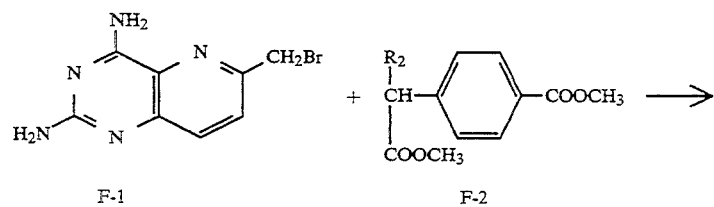

-continued
Scheme F

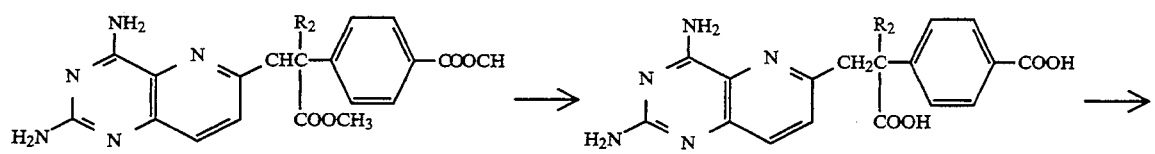

F-3 → F-4

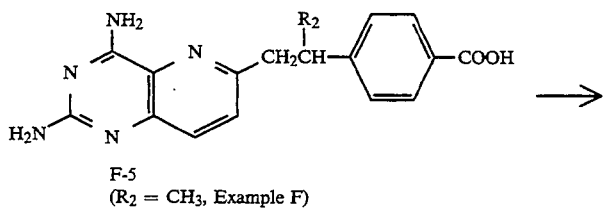

F-5
($R_2$ = $CH_3$, Example F)

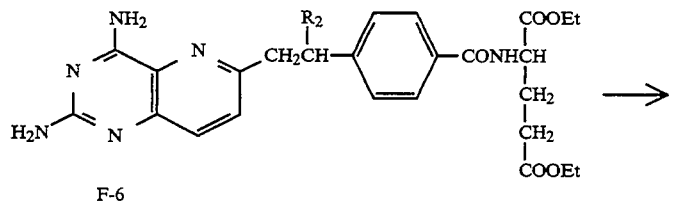

F-6

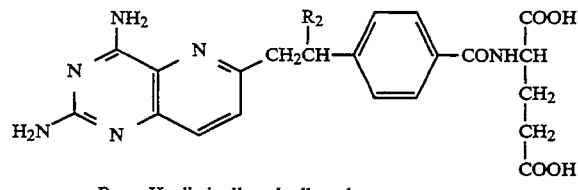

$R_2$ = H, alkyl, alkenyl, alkynyl

In accordance with the present invention, a synthesis is provided for the preparation of 10-deazaaminopterins and 5,10- and 8,10-dideazaaminopterins.

The first stage of the synthesis, which is believed to be novel in itself, is shown in Scheme 1A:

Y is selected from the group consisting of N and $CR_3$, where $R_3$ is hydrogen, alkyl of from one to about eight carbon atoms or chlorine;

Z is N or CH $R_1$ is selected from the group consisting of alkyl,

Scheme 1A

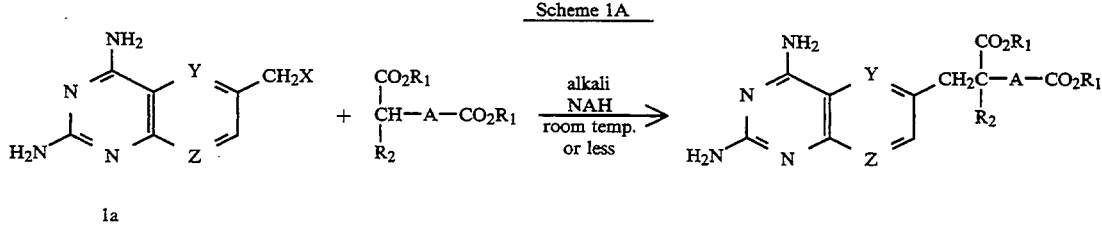

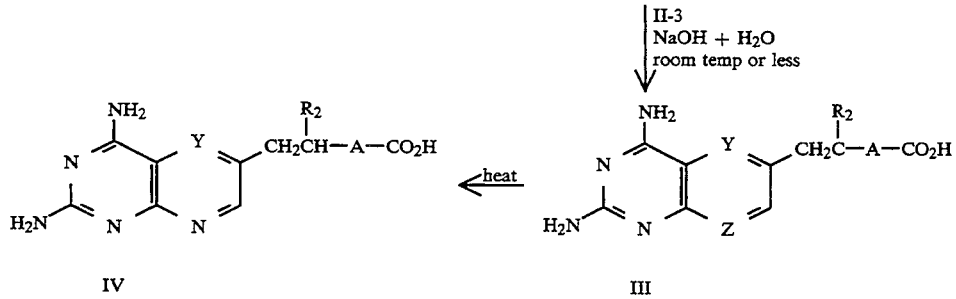

wherein:

X is halogen, such as chlorine, bromine or iodine;

cycloalkyl, and alkaryl having from one to about twelve carbon atoms;

$R_2$ is selected from the group consisting of alkyl, alkenyl, alkynyl, aralkyl, and heteroalkyl having from one to about twenty carbon atoms; and A is selected from the group consisting of aryl and heteroaryl having from two to about twenty carbon atoms and up to three hetero atoms selected from nitrogen, oxygen, and sulfur.

In this stage, the 6-methylene halide of the selected deazaaminopterin nucleus Ia is coupled with the selected diester Ic having the desired A group, with alkali metal hydride such as NaH or KH is a polar solvent that is inert to the reactants such as dimethyl sulfoxide, N-methyl pyrrolidone, glycol ethers such as diethylene glycol or methoxyethylene glycol, tetrahydrofuran, or lower aliphatic alcohols such as methanol or ethanol. Alkali metal hydroxides such as sodium hydroxide and potassium hydroxide and alkali metal alkoxides, such as sodium or potassium ethoxide can be substituted for the alkali metal hydride. In some cases, strong amine bases such as trimethylamine can be used.

The coupling proceeds at low temperatures; there is no critical lower limit, except that the reaction mixture should remain fluid at the reaction temperature. Temperatures as low as $-30°$ C. have been used. However, the temperature should not usually exceed room temperature, such as 25° C., to minimize side reactions and decomposition of reaction products.

The starting diester 1c, if not available, can be prepared by carbonation of the corresponding acid ester 1b.

The diester of the pteroic acid II is then hydrolyzed to the corresponding diacid III by alkali metal hydroxide in aqueous or aqueous alcoholic medium, also at a temperature below about 25° C., i.e., room temperature. The hydrolyzed reaction product is then precipitated by addition of strong inorganic or organic acid such as hydrochloric, sulfuric or acetic acid to a pH within the range from about 4 to about 6.5, preferably from 5 to 6, formation of the amine salt, which might interfere with the next step, monodecarboxylation of the diacid III to the monoacid IV.

Instead of aqueous solvents, polar organic solvents in which the reactants are soluble, such as dimethyl sulfoxide or acetonitrile, can also be used. In this case, precipitation may be effected by solvent evaporation or removal.

The monodecarboxylation is carried out at an elevated temperature at which the reaction proceeds, but below that at which decomposition of reaction product occurs. Usually, temperatures within the range from about 100° C. to about 150° C. are satisfactory but temperatures as low as 25° C. and as high as 200° C. have been used with good results.

The monodecarboxylation can be applied to the solid diacid or in solution in a polar solvent, such as dimethyl sulfoxide. Pressure can be used to maintain the solvent liquid if the temperature is to exceed its boiling point.

The ester hydrolysis and decarboxylation steps represent a considerable improvement over the prior procedure using NaCN in dimethylsulfoxide to cleave the ester groups of II and monodecarboxylate III, proceeding directly without isolating III to form IV. This requires considerably higher temperatures, even exceeding 180°–200° C., giving poor yields of dark-colored products.

The second stage of the synthesis proceeds using known steps from the monocarboxylic acid IV to the corresponding 10-deazaaminopterin or 5,10- or 8,10-dideazaaminopterin, and is shown in Scheme 1B.

Scheme 1B

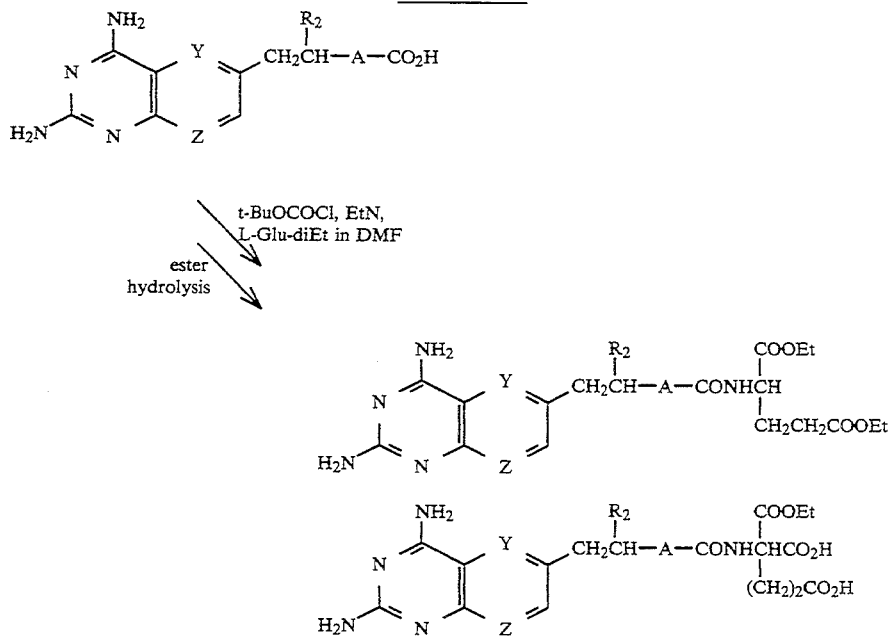

The details for these steps are shown in U.S. Pat. No. 4,433,147 patented Feb. 21, 1984, the disclosure of which is hereby incorporated by reference, and therefore will not be repeated here.

Schemes A to F illustrate application of the general reaction scheme above to the preparation of the specific compounds of Examples A, B, C, D, E, and F, the details of the preparation of which are given in the Examples following.

The following Examples in the opinions of the inventors represent preferred embodiments of the process of this invention.

EXAMPLE A

α-Allyhomoterephthalic Acid Dimethyl Ester (A-1). A mixture of 35% potassium hydride oil suspension (6.04 g, 35% w/w, 53 mmols of potassium hydride) in 240 mL of sieve dried tetrahydrofuran was cooled to 0° C. The cold mixture was treated with homoterephthalic acid dimethyl ester (10.0 g, 48 mmols). The mixture was stirred at 0° C. for 1 hour. Allyl bromide (6.41 g, 53 mmols) was added and the mixture stirred at 0° C. for 30 min, then at room temperature for 16 hours. The resulting mixture was treated with 4.8 mL of 50% acetic acid, then poured into 480 mL of water. The mixture was extracted with ether (2×250 mL). The ether extracts were combined, dried over magnesium sulfate, and concentrated to a brown oil. Chromatography on 250 g of flash silica gel (10% ether in hexane eluent) gave the product as a pale yellow oil, 10.5 g (89% yield). $^1$H NMR (CDCl$_3$): δ=7.69 (q, 4H, Ar); 5.64 (m, 1H, CH=CH$_2$); 5.09 (m, 2H, CH$_2$=CH); 3.80 (m, 7H, 2×CH$_3$O≠ArCH); 2.75 (m, 2H, CH$_2$CHAr).

10-Allyl-10-carbomethoxy-4-deoxy-4-amino-10-deazapteroic Acid Methyl Ester (A-2). A mixture of potassium hydride in oil (2.43 g, 35% w/w, 21.2 mmols) in dry dimethylformamide (25 mL) was cooled to −5° C. The cold mixture was treated, dropwise, with a solution of α-allylhomoterephthalic acid dimethyl ester (A-1) (5.25 g, 21.2 mmols) in dry dimethylformamide (25 mL) then stirred at 0° C. for 45 minutes. After cooling to −20° C., a solution of 2,4-diamino-6-bromomethylpteridine hydrobromide.0.2 isopropanol (2.45 g, 7.06 mmols) in dry dimethylformamide (40 mL) was added dropwise, maintaining a −20° C. reaction temperature. The temperature was allowed to rise to 20° C. and was stirred for 2.5 hours. The reaction was then adjusted to pH 7 by addition of solid carbon dioxide. Concentration under high vacuum gave a residue which was dissolved in chloroform. This solution was washed with water, dried, and concentrated. The residue was washed with ether and dried in vacuo giving 2.2 g of product (74% yield). Thin layer chromatography (10% methanol in chloroform on silica gel plates) showed a single spot, Rf 0.4. Mass spectrum m/e 423 (M+H). $^1$H NMR (CDCl$_3$): 8.45 (2, 1H, 7-H); 8.03 (d, 2H, C$_6$H$_4$); 7.37 (d, 2H, C$_6$H$_4$); 5.50 (m, CH=CH$_2$); 4.95 (m, 2H, CH$_2$=CH); 3.90 (s, 3H, ArCOOCH$_3$); 3.60 (m, 5H, C-10 COOCH$_3$-C-9 CH$_2$); 2.83 (m, 2H, CH$_2$CH=CH$_2$)

10-Allyl-10-carboxy-4-deoxy-4-amino-10-deazapteroic Acid (A-3). A solution of the dimethyl ester (A-2) (2.0 g, 4.7 mmols) in 2-methoxyethanol (2 mL) was treated with water (2 mL) then 10% sodium hydroxide (2 mL). The solution was stirred at room temperature for 24 hours. The solution was adjusted to pH 6 with acetic acid and concentrated under high vacuum to give a residue which was then dissolved in water (10 mL). Further acidification to pH 3 resulted in a precipitate which was collected, washed with water and dried in vacuo to yield 1.53 g of yellow solid (81%). HPLC (25% methanol in 0.1 molar monobasic sodium phosphate, pH 6.5, Novapak C$_{18}$ radial compression column) indicated 90% purity. Mass spectrum m/e 395 (M+H); UV (0.1N NaOH): λmax 255 nm (28,194), 368 (7,444).

10-Allyl-4-deoxy-4-amino-10-deazapteroic Acid (A-4) (Example A). A solution of the dicarboxylic acid (IIIa) (0.26 g) in dry dimethyl sulfoxide (10 mL) was placed in a pre-heated 142° C. oil bath for 10 minutes. The solution was cooled to 35° C. and concentrated under high vacuum. The residue was triturated with ether to yield a tan solid, 0.23 g, 99% yield. HPLC (Novapak C$_1$ radial compression column, 25% methanol in 0.1 molar monobasic sodium phosphate, pH 6.5) indicated 95% purity. Mass spectrum m/e 351 (M+H).

EXAMPLES B TO D

α-Propargylhomoterephthalic Acid Dimethyl Ester (B-1) Example B, Scheme B, Compound B-4. A mixture of 35% potassium hydride in oil (6.04 g, 35% w/w, 53 mmols of potassium hydride) in 240 mL of sieve dried tetrahydrofuran was cooled to 0° C. The cold mixture was treated with homoterephthalic acid dimethyl ester (10.0 g, 48 mmols). The mixture was stirred at 0° C. for 1 hour. Propargyl bromide (53 mmols) was added and the mixture stirred at 0° C. for 30 min, then at room temperature for 16 hours. The resulting mixture was treated with 4.8 mL of 50% acetic acid, then poured into 480 mL of water. The mixture was extracted with ether (2×250 mL). The ether extracts were combined, dried over magnesium sulfate, and concentrated to a brown oil. Chromatography on 250 g of flash silica gel (10% ether in hexane eluent) gave the product as a white solid mp 63°-65° C. Mass spectrum m/e 247 (M+H). IR (nujol C≡C—H, 3268 cm$^{-1}$. $^1$H NMR (CDCl$_3$): δ 8.05 (d, 2H, C$_6$H$_4$); 7.04 (d, 2H, C$_6$H$_4$); 3.91 (s, 3H, ArCOOCH$_3$); 3.88 (dd, 1H, ArCH); 3.71 (s, 3H, —CHCOOCH$_3$); 2.95 (dddd, 1H, CH$_2$); 2.64 (dddd, 1H, CH$_2$); 1.96 (dd, 1H, C≡CH). Anal. Calcd for C$_{14}$H$_{14}$)$_4$: C, 68.3; H, 5.73. Found: C, 68.0; H, 5.60.

10-Propargyl-10-carbomethoxy-4-deoxy-4-amino-10-deazapteroic Acid Methyl Ester (B-2). A mixture of potassium hydride (2.43 g, 35% w/w, 21.2 mmols) in dry dimethylformamide (25 mL) was cooled to −5° C. The cold mixture was treated dropwise, with a solution of propargylhomoterephthalic acid dimethyl ester (B-1) (21.2 mmols) in dry dimethylformamide (25 mL) then stirred at 0° C. for 45 minutes. After cooling to −20° C., a solution of 2,4-diamino-6-bromomethylpteridine hydrobromide.0.2 isopropanol (2.45 g, 7.06 mmols) in dry dimethylformamide (40 mL) was added dropwise, maintaining a −20° C. reaction temperature. The temperature was allowed to rise to 20° C. and was stirred for 2.5 hours. The reaction was then adjusted to pH 7 by addition of solid carbon dioxide. Concentration under high vacuum gave a residue which, however, was not soluble in common organic solvents, and was therefore carried unpurified into the next step. The purity was acceptable by thin layer chromatographic analysis. The crude weight recovery was 90%. Mass spectrum m/e 420.

10-Propargyl-10-carboxy-4-deoxy-4-amino-10-deazapteroic Acid (B-3). A solution of the dimethyl ester (B-2) (4.7 mmols) in 2-methoxyethanol (2 mL) was treated with water (2 mL) then 10% sodium hydroxide (2 mL). The solution was stirred at room temperature for 24 hours. The solution was adjusted to pH 6 with acetic acid and concentrated under high vacuum to give a residue which was then dissolved in water (10 mL). Further acidification to pH 6 resulted in a precipitate which was collected, washed with water and dried in vacuo. HPLC analysis indicated 92% purity after reprecipitation of the product from basic solution. The product was obtained as a white solid in 75% yield. Mass spectrum m/e 680 (M-H as the TMS$_4$ derivative).

10-Propargyl-4-deoxy-4-amino-10-deazapteroic Acid (B-4) (Example B). Three decarboxylations of B-3 were conducted on 86, 86, and 55 mg of material. In each use the reaction aliquot was dissolved in 3 mL of dimethyl sulfoxide and immersed for a period of five minutes in an oil bath preheated to 123° C. The reactions were combined and the solvent removed in high vacuum. The residue was precipitated twice from dilute ammonium hydroxide solution by addition of acetic acid. HPLC analysis indicated 85% purity with no impurity exceeding 4%. The product was a tan solid (29% yield). Mass spectrum 564 (M+H as the $TMS_3$ derivative).

10-Carbomethoxy-4-deoxy-4-amino-5,10-dideazapteroic Acid Methyl Ester (Example C, Scheme C, Compound C-5) (C-3, $R_1=R_2=H$). NaH (4.80 mg of 60% dispersion in oil, 12.0 mmol) was suspended in DMF (9 mL), and the mixture was chilled to 0° C., then treated with a solution of homoterephthalic acid dimethyl ester (2.5 g, 12 mmol) in DMF (9 mL). After 0.5 h at 0° C., the stirred mixture was chilled to −25° C., treated with a solution of C-4, $R_1=H$ [J. Piper et al., J. Med. Chem. 35, 332 (1992)](1.25 g, 3 mmol) in DMF (9 mL), and allowed to warm to −10° C. After 2.5 h at −10°±5° C., the pH was adjusted to 7.0 by using small pieces of solid $CO_2$. The solvent was removed in vacuo, and the residue was suspended between $H_2O$ (100 mL) and $CHCl_3$ (375 mL). The aqueous layer was then extracted twice with $CHCl_3$ (375 mL each). The $CHCl_3$ phases were pooled, dried over $Na_2SO_4$, and evaporated. The residue was dissolved in $CHCl_3$-MeOH (7:1) and applied to a column of silica gel in $CHCl_3$-MeOH, 7:1, the same solvent system. Homogeneous fractions were pooled, evaporated, and dried to a light yellow solid (611 mg, 54% yield). Homogeneous on TLC (Rf=0.44; $CHCl_3$-MeOH, 7:1). MS, m/e 382, $(M+H)^+$.

10-Carboxy-4-deoxy-4-amino-5,10-dideazapteroic Acid (C-4, $R_1=R_2=H$). Compound C-3 (5.50 mg, 1.44 mmol) in DMSO (25 mL) was treated with 1N NaOH (3.5 mL). The reaction flask was flushed with $N_2$, and the mixture was stirred at 20°–25° C. for 24 h. After the solvent had been removed by short-path distillation in vacuo (bath to 40° C.), the residue was dissolved in $H_2O$ (30 mL) and the filtered solution was acidified by using glacial AcOH to pH 5.0. The resulting gel was frozen (dry ice acetone bath), then thawed (in a refrigerator at 3° C.), leaving a particulate solid, that was collected, washed with $H_2O$, and dried in vacuo (25° C., $P_2O_5$), yielding 442 mg (82% yield); MS, m/e 354, $(M+H)^+$. Anal. Calcd. for $C_{17}H_{15}N_5O_4$. 1.25 $H_2O$: C, 54.3; H, 4.69; N, 18.6. Found: C, 54.2; H, 4.41; N, 18.6.

4-Deoxy-4-amino-5,10-dideazapteroic Acid (C-5, $R_2=R_2=H$, Example C). Progress of the decarboxylation of C-4 (384 mg, 1.08 mmol) in dry DMSO (15–20 mL) under $N_2$ at 160°–164° C. was monitored by $CO_2$ evaluation, which stopped after 20 min. The DMSO was removed by short-path distillation in vacuo (bath to 40° C.), and the residue was stirred with $H_2O$, collected, and dried in vacuo (25° C., $P_2O_5$). Mass spectral analysis indicated the crude product to consist of the desired C-5 and a contaminant of molecular weight 369. The contaminant proved to be insoluble in 1N NaOH and was removed by filtration after the crude product mixture had been stirred with sufficient 1N NaOH to dissolve C-5. The product was then precipitated by acidification to pH 5.0–5.5 by adding 1N HCl. The resulting mixture gelled, but after being frozen and then allowed to thaw slowly, the precipitate changed to particulate matter and was collected, washed with $H_2O$, and dried in vacuo (25° C., $P_2O_5$) to give C-5 in 72% yield (253 mg). MS, m/e 310, $(M+H)^+$. Anal. Calcd. for $C_{16}H_{15}N_5O_2$. $H_2O$: C, 58.7; H, 4.93; N, 21.4. Found: C, 58.3; H, 4.76; N, 21.0.

2-Carboxythiophene-5-acetic Acid Dimethyl Ester Example D, Scheme D, Compound D-5 (D-2, $R_2=H$). Freshly distilled diisopropylamine (24.6 g, 0.24 mol) in 250 mL of dry THF was cooled to 0° C. under argon then treated dropwise with 98 mL (2.24 mol) of 2.5M BuLi in hexane. After 1 h, the LDA solution was added dropwise with stirring to a −30° mixture of 15.0 g(0.11 mol) of 5-methylthiophene- 2-carboxylic acid (D-1) in 300 mL of dry THF. The temperature of the resulting red solution was allowed to rise 0° C. and was so maintained for another 2 h. Carbon dioxide was bubbled through the solution to produce a yellow precipitate. The mixture was stirred at ambient temperature for 2 h and filtered. The yellow filter cake was suspended in 300 mL of MeOH, and the mixture was cooled to 0° C. and treated with 100 mL of MeOH saturated with dry HCl. The mixture was stirred at room temperature for 72 h, concentrated in vacuo and the residue was partitioned between $Et_2O$ (500 mL) and 250 mL of sat'd $NaHCO_3$. The $Et_2O$ extract was washed with $H_2O$ (3×250 mL), dried over $MgSO_4$ and evaporated to leave a dark oil (15 g). Chromatography on flash silica gel (EtOAc-hexane, 1:19) gave 11.4 g of the product (51%) as a white, waxy solid; NMR ($CDCl_3$) δ 7.61 (d, 1H, 3-H); 6.90 (d, 1H, 4-H); 3.87 (m, 5H, Ar-$COOCH_3+CH_2$); 3.82 (s, 3H, $CH_2COOCH_3$); Anal. ($C_9H_{10}O_4S$). Calcd. C, 50.5; H, 4.71. Found, C, 50.6; H, 4.79.

Methyl 5-(α-Carbomethoxy-β-2,4-diamino-6-pteridinyl)ethylthiophene-2-carboxylate (D-3, $R_2=H$). A suspension of 50% sodium hydride in oil (0.84 g, 17.5 mmol of sodium hydride) in 15 mL of dry dimethyl formamide was cooled to 0° C. A solution of the diester (D-2, 3.73 g, 17.4 mmol) in 15 mL of dry dimethyl formamide was added dropwise. The resulting mixture was stirred at 0° C. for 1 h then cooled to −30° C. and treated with a solution of 2,4-diamino-6-bromomethyl pteridine hydrobromide (16.1 mmol) in 40 mL of dry dimethyl formamide. The resulting mixture was stirred for 2.5 h while rising to room temperature, then neutralized (pH 7.5) by adding solid carbon dioxide. The mixture was concentrated under high vacuum, and the residue was washed with ether, then water, and dried under high vacuum to give the product as a yellow solid (1.98 g, 88%); MS 389 (M+H); NMR ($d_6$DMSO) δ 8.58 (s, 1H, $C_7$-H); 7.60 (m, 3H, $C_3$'-H+$NH_2$); 7.12 (d, 1H, $C_4$'-H); 6.61 (broad s, 2H, $NH_2$); 4.9 (t, 1H, $C_{10}$-H); 3.75 (s, 3H, $C_2$'-$COOCH_3$); 3.63 (m, 5H, $C_{10}$-$COOCH_3+C_9$-$H_2$).

5-(α-Carboxy-β-2,4-diaminopteridinyl)ethylthiophene-2-carboxylic Acid (D-4, $R_2=H$). A solution of the diester (D-3b, 1.96 g, 5.05 mmol) in 30 mL of 2-methoxy ethanol, water, and 30 mL of 2.5 N NaOH was stirred for 1.5 h. The mixture was filtered, and the filtrate was neutralized (pH 7) with HOAc and concentrated under high vacuum. The residue was suspended in water (30 mL) and adjusted with HOAc to pH 5 to produce a precipitate. Filtration gave a tan solid that was digested in 95% EtOH and filtered to give a tan solid that was washed with $Et_2O$ and dried in vacuo, yielding 1.31 g (77%) of product; HPLC showed 92.2% purity; NMR ($d_6$DMSO) δ 8.51 (s, 1H, $C_7$-H); 7.55 (broad s, 2H, $NH_2$); 7.17 (d, 1H, 3'-H); 6.81 (d, 1H, 4'-H); 6.55 (broad s, 2H, $NH_2$); 4.40 (t, 1H, $C_{10}$-H); 3.15 (m, 2H, $C_9$-$H_2$).

5-(β-2,4-Diamino-6-pteridinylethylthiophene-2-carboxylic Acid (D-5, $R_2=H$). A solution of the dicarboxylic acid (D-4, 1.31 g, 3.64 mmol) in argon purged DMSO was placed in a 135° C. oil bath for 45 min. The solution was then concentrated under high vacuum to a residue that was digested in Et$_2$O (50 mL). Filtration yielded a brown solid that was washed with ether and dried in vacuo to give 1.31 g of crude product. The material was suspended in water (75 mL) and treated dropwise with 1.5N NH$_4$OH to pH 12. Insoluble material was removed by filtration and the filtrate adjusted to pH 5 with HOAc to give a precipitate. Filtration gave a brown solid that was washed with H$_2$O and dried in vacuo, yielding 0.97 g product (84%); UV (0.1N NaOH) 257 nm ($\epsilon$25,305), 372 (6,491); Anal. (C$_{13}$H$_{12}$N$_6$O$_2$S.H$_2$O). Calc. C, 46.7; H, 4.22; N, 25.1. Found c, 46.8; H, 4.01; N.24.8.

EXAMPLE E. SCHEME E. COMPOUND E-5, $R_1=CH_3$, $R_2=H$ AND EXAMPLE F

5-Carbomethoxy-2-pyridylacetic Acid Methyl Ester (E-2, $R_2=H$). Freshly distilled diisopropylamine (7.4 g, 73 mmol) in dry tetrahydrofuran (100 mL) was cooled under argon to 0° C. then treated dropwise with n-butyl lithium in hexanes (50 mL of a 1.6-M solution) and stirred at 0° for 1 h. The lithium diisopropyl amide solution was added dropwise over 45 min to a $-25°$ C. mixture of 6-methylnicotinic acid (4.0 g, 29 mmol) and hexamethylphosphorous triamide (5.23 g) in dry tetrahydrofuran. The temperature of the red solution was allowed to rise to 0° C. whereupon stirring was continued for 2 h. Carbon dioxide was bubbled through the 0° C. solution, resulting in a yellow precipitate. The mixture was allowed to rise to room temperature and was stirred for 16 h. Filtration gave a yellow solid that was suspended in methanol (50 mL), and the mixture was cooled to 0° C. Saturated methanolic hydrogen chloride (50 mL) was added, and the solution was stirred at room temperature for 72 h. Concentration in vacuo gave a residue that was partitioned between ether and saturated sodium bicarbonate. The ether layer was washed with water, dried over magnesium sulfate, and concentrated to an orange oil. Chromatography on flash silica gel (5% ethyl acetate in hexanes) gave the product as a yellow solid, 1.84 g (30%); m.p. 56°–57°; NMR (CDCl$_3$): $\delta$ 9.10 (m, 1H, 6-H); 8.21 (m, 1H, 4-H); 7.33 (m, 1H, 3-H); 3.84 (m, 8H, CH$_2$COOCH$_3$+Ar-COOCH$_3$). Anal. (C$_{10}$H$_{11}$NO$_4$). Calc.: C,57.4; H,5.30; N,6.70. Found: C,57.5; H,5.33; N,6.54.

10-Carbomethoxy-4-deoxy-4-amino-5-methyl-5,10-dideaza-3'-azapteroic Acid Methyl Ester (E-3, $R_1=CH_3$, $R_2=H$). NaH (480 mg of 60% in oil, 12.0 mmol) was suspended in DMF (12 mL), and the mixture was chilled to 0° C., then treated with a solution of 3-carbomethoxy-6-pyridylacetic acid methyl ester (E-2, $R_2=H$, 2.50 g, 12.0 mmol) in DMF (12 mL). After 0.5 h at 0° C., the stirred mixture was chilled to $-25°$ C., treated with a solution of 2,4-diamino-5-methyl-6-bromomethyl-5-deazapteridine [J. Piper et al., J. Med. Chem. 35, 332 (1992)].1.7HBr.0.5AcOH (1.71 g, 3.92 mmol) in DMF (12 mL), then allowed to warm to $-10°$ C. After 1 h at near $-10°$ C., the solution was allowed to warm to ambient temperature. After 1 h at 20°–23° C., the mixture was neutralized by the addition of small pieces of solid CO$_2$. Addition of silica gel (7.5 g of 60-200 mesh) followed, and the resulting mixture was evaporated to dryness (<1 mm, bath to 40° C.) to give a dispersion of crude product in silica gel which was applied to a column of silica gel. Elution by CHCl$_3$-MeOH (9:1) led to fractions homogeneous in E-3 according to TLC (CHCl$_3$-MeOH, 3:1; Rf~0.6). Evaporation of the combined fractions gave E-3 in 43% yield (668 mg); mass spectrum, m/e 397, MH+ for C$_{19}$H$_{20}$N$_6$O$_4$.

10-Carboxy-4-deoxy-4-amino-5-methyl-5,10-dideaza-3'-azapteroic Acid (E-4, $R_1=CH_3$, $R_2=H$). A suspension of E-3 (668 mg, 1.69 mmol) in DMSO was treated with 4N NaOH (1.0 mL). The resulting clear solution was kept under N$_2$ in a stoppered flask protected from light for 20 h. After the solvent had been removed by short-path distillation in vacuo (<1 mm, bath to 40° C.) the residue was dissolved in H$_2$O (30 mL), and the filtered solution was acidified to pH5 using glacial AcOH. The mixture was kept several hours in a refrigerator before the solid was collected, washed with H$_2$O, and dried in vacuo to give 594 mg. This material was found through HPLC assay results and mass spectral data to be a mixture consisting of 88 % compound E-4 (m/e 369, MH+ for C$_{17}$H$_{16}$N$_6$O$_4$) and 12% of the sequential product III-10 (m/e 325, MH+ for C16H16N6O2). The weight of the mixture (594 mg) corresponds to conversion of 97% of E-3.

4-Amino-4-deoxy-5-methyl-5,10-dideaza-3'-azapteroic Acid (E-5, $R_1=CH_3$, $R_2$-H) (Example E). The above product mixture (594 mg, predominantly E-4 with some E-5) was suspended in DMF (15 mL), and the stirred mixture was kept at 60°–65° C. for 12 min. Decarboxylation was slow at this temperature, and the bath was raised to 80°–85° C. Heating was continued 15 min longer. To ensure complete reaction, DMF was removed in vacuo and replaced with DMSO. The resulting clear solution was kept at 60°–65° C. for 15 min, then examined by HPLC. All E-4 had been converted to E-5. DMSO was removed in vacuo, and the product was precipitated from a clarified (Norit, Celite) solution of its Na salt by addition of AcOH to pH 5; yield 77% (443 mg) of E-5.1.5H$_2$O. Mass spectrum, m/e 325, MH$^{30}$. Anal. Calcd for C$_{16}$H$_{16}$N$_6$O$_2$: C, 54.69; H, 5.45; N, 23.92. Found: C, 54.77, 54.70; H, 5.13, 5.20; N, 24.41, 24.47.

α-Methylhomoterephthalic Acid Dimethyl Ester (F-2, $R_2=CH_3$). A mixture of 35% potassium hydride in oil (6.04 g, equivalent to 2.11 g, 53 mmol of potassium hydride) in 240 mL of sieve dried tetrahydrofuran was cooled to 0° C. The cold mixture was treated with homoterephthalic acid dimethyl ester (10.0 g, 48 mmol). The mixture was stirred at 0° C. for 1 h. Methyl iodide (7.51 g, 53 mmol) was added and the mixture stirred at 0° C. for 30 min, then at room temperature for 16 h. The resulting mixture was treated with 4.8 mL of 50% acetic acid, then poured into 480 mL of water. The mixture was extracted with ether (2×250 mL). The ether extracts were combined, dried on magnesium sulfate, and concentrated to a brown oil, 15.67 g. Chromatography on 250 g of flash silica gel (10% ether in hexanes eluent) gave the product as a pale yellow oil, 7.24 g (67.9% theory). NMR (CDCl$_3$): $\delta$=7.56 (q, 4H, Ar); 2.78 (m, 7H, 2×CH$_3$O+ArCH); 1.49 (d, 3H, CH$_3$CH).

10-Methyl-10-carbomethoxy-4-deoxy-4-amino-8,10-dideazapteroic Acid Methyl Ester (F-3, $R_2=CH_3$). Potassium hydride (3.0 g of 35%, equivalent to 26.2 mmol hydride) in dry dimethyl formamide (19 mL) was cooled to 0° C. To the cold suspension was added α-methylhomoterephthalic acid dimethyl ester (F-2) (5.8 g, 26.2 mmol) in dry dimethylformamide (20 mL). The yellow-orange mixture was stirred an additional 30 min at 0° C. The reaction mixture was then cooled to $-25°$ C. and 6-bromomethyl-2,4-diamino-8-deazapteridine hydrobromide (F-1) (2.8 g, 8.3 mmol) in dry dimethylformamide (40 mL) was added dropwise. The temperature was allowed to rise to −10° C. After 2.5 h, the reaction mixture was adjusted to pH=7 by adding solid carbon dioxide. The mixture was concentrated under high vacuum and the residue shaken in 100 mL of chloroform and water. The organic layer was separated, and the aqueous was again extracted with 50 mL of chloroform. The organics were combined, dried on magnesium sulfate, and concentrated. Chromatography of the residue on flash silica gel (chloroform, then 5% methanol in chloroform, then 10% methanol in chloroform) gave 1.5 g of product (44%), which was homogeneous by thin-layer chromatography, $R_f=0.4$.

10-Methyl-10-carboxy-4-deoxy-4-amino-8,10-dideazapteroic Acid (F-4, $R_2=CH_3$). 10-Methyl-10-carbomethoxy-4-deoxy-4-amino-8-deazapteroic acid methyl ester (F-3) (1.5 g, 3.8 mmol) in 2-methoxyethanol (15.5 mL) was treated with 10% sodium hydroxide (15.5 mL), then water (15.5 mL). The mixture was stirred at room temperature for 24 h. The pH was adjusted with four normal hydrochloric acid to pH=4. Filtration gave a white solid that was washed with water. After drying in vacuo at 50° C., 1.0 g of F-4 was obtained as a white solid (71.7%). HPLC showed 96.2% purity.

10-Methyl-4-deoxy-4-amino-8,10-dideazapteroic Acid (F-5, $R_2=CH_3$, Example F). 10-Methyl-10-carboxy-4-deoxy-4-amino-8,10-dideazapteroic acid (F-4) (0.92 g, 2.5 mmol) in dry, argon purged dimethyl sulfoxide (20 mL) was warmed in a 180° C. oil bath for 10 min. The mixture was then concentrated under high vacuum. The residue was washed with water and dried in vacuo at 55° C. yielding 0.76 g of product (94.1% theory). HPLC showed 97% purity. NMR (d$_6$-DMSO): $\delta$=7.83 (m, 2H, C$_6$H$_4$); 7.35 (m, 6H, C$_6$H$_4$+7-H+8-H+NH$_2$); 6.27 (br s, 2H, NH$_2$); 3.50 (m, 2H, 9-H$_2$); 3.07 (m, 1H, 10-H); 1.23 (d, 3H, 10-CH$_3$).

The 10-deazaaminopterin or 5,10- or 8,10-dideazaaminopterin compound can be administered per se, or in association with a pharmaceutically acceptable diluent or carrier. The invention accordingly also provides a pharmaceutical composition in dosage unit form comprising from 0.1 to about 500 mg of 10-deazaaminopterin or 5,10- or 8,10-dideazaaminopterin compound, per dosage unit, together with a pharmaceutically acceptable nontoxic inert carrier or diluent therefor.

The 10-deazaaminopterin or 5,10- or 8,10-dideazaaminopterin compound can be used as such, or in the form of an acid addition salt. These salts are formed with one or more free NH$_2$ groups of the 10-deazaaminopterin or 5,10- or 8,10-dideazaaminopterin molecule. Typically, the compounds are injected in the form of their sodium salts in aqueous solution. Other salts, e.g., K, Ca, NH$_4$, et. could be used as prepared from the appropriate hydroxide or carbonates.

The acid addition salts are preferably the pharmaceutically acceptable, nontoxic addition salts with suitable acids, such as those with inorganic acids, for example, hydrochloric, hydrobromic, nitric, sulphuric and phosphoric acids, and with organic acids, such as organic carboxylic acids, for example, glycolic, maleic, hydroxymaleic, malic, tartaric, citric, salicylic, acetyloxybenzoic, nicotinic and isonicotinic acid, and organic sulphonic acids, for example, methanesulphonic, ethanesulphonic, 2-hydroxyethanesulphonic, toluene-p-sulphonic, and naphthalene-2-sulphonic acid.

An acid addition salt can be converted into the free compound according to known methods, for example, by treating it with a base such as with a metal hydroxide or alkoxide, for example, an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example, sodium, potassium or calcium carbonate or hydrogen carbonate, with ammonia; or with a hydroxyl ion exchange resin, or with any other suitable reagent.

An acid addition salt may also be converted into another acid addition salt according to known methods, for example, a salt with an inorganic acid may be treated with a metal salt, for example a sodium, barium or silver salt, of an acid in a suitable diluent, in which a resulting inorganic salt is insoluble and is thus removed from the reaction medium. An acid-addition salt may also be converted into another acid addition salt by treatment with an anion exchange preparation.

The glutamic acid COOH groups can also be in salt form, as the ammonium NH$_4$, alkali metal salts (Na$^+$, K$^+$) or the nontoxic alkaline earth metal salts (Ca$^{++}$) of the glutamate COOH groups.

The 10-deazaaminopterin or 5,10- or 8,10-dideazaaminopterin compound or salt thereof can be administered to the animal by any available route, including oral and parenteral (intravenous, intraperitoneal, subcutaneous, and intramuscular) adminstration. The amount administered is sufficient to ameliorate the arthritis or other proliferative disease, and will depend upon the type of arthritis, the species of animal, and the weight of the animal. For example, in human administration, a dosage of 10-deasaaminopterin or 5,10- or 8,10-dideazaaminopterin compound within the range from about 0.1 mg/kg to about 500 mg/kg per day should be sufficient. Dosages in the higher part of the range, approaching 500 mg/kg, are normally administered in conjunction with leucovorin (dl-r-formyl tetrahydofolate) to reduce toxicity. In the treatment of lower test animals, a similar dosage range is therapeutic. The upper limit of dosage is that imposed by toxic side effects, and can be determined by trial and error for the animal to be treated, including humans.

To facilitate administration, the 10-deazaaminopterin or 5,10or 8,10-dideazaaminopterin compound or salt thereof can be provided in composition form, and preferably in dosage unit form. While the compound can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the 10-deazaaminopterin or 5,10- or 8,10-dideazaaminopterin compound. Exemplary diluents and carriers inlcude lactose, dextrose, sucrose, sorbitol, mannitol, starches, gun acacia, calcium phosphate, mineral oil, cocoa butter, oil of theobroma, alginates, tragacanth, prophydroxybenzoate, talc or magnesium stearate.

For convenience in handling, the 10-deazaaminopterin or 5,10- or 8,10-dideazaaminopterin compound and carrier or diluent can be enclosed or encapsulated in a capsule, sachet, cachet, gelatin, paper or other container, especially when intended for use in dosage units. The dosage units can for example take the form of tablets, capsules, suppositories, or cachets.

The following Examples illustrate various forms of dosage units in which the 10-deazaaminopterin or 5,10- or 8,10-dideazaaminopterin compounds or salts thereof can be prepared:

EXAMPLE 1

| Tablet Formation | Mg/tablet |
| --- | --- |
| 10-deazaaminopterin or 5,10- or 8,10-dideazaaminopterin compound | 15 |
| Lactose | 86 |
| Corn starch (dried) | 45.5 |
| Gelatin | 2.5 |
| Magnesium stearate | 1.0 |

The 10-deazaaminopterin or 5,10- or 8,10-dideazaaminopterin compound is powdered and passed through a mesh sieve and well mixed with the lactose and 30 mg of the corn starch, both passed through a sieve.

The mixed powders are massed with a warm gelatin solution, prepared by stirring the gelatin in water and heating to form a 10% w/w solution. The mass is granulated by passing through a sieve, and the moist granules dried at 40° C.

The dried granules are regranulated by passing through a sieve and the balance of the starch and the magnesium stearate is added and thoroughly mixed.

The granules are compressed to produce tablets each weighing 150 mg.

EXAMPLE 2

| Tablet Formation | Mg/tablet |
| --- | --- |
| 10-deazaaminopterin or 5,10- or 8,10-dideazaaminopterin compound | 100 |
| Lactose | 39 |
| Corn starch (dried) | 80 |
| Gelatin | 4.0 |
| Magnesium stearate | 2.0 |

The method of preparation is identical with that of Example 1 except that 60 mg of starch is used in the granulation process and 20 mg during tableting.

EXAMPLE 3

| Capsule formation | Mg/capsule |
| --- | --- |
| 10-deazaaminopterin or 5,10- or 8,10-dideazaaminopterin compound | 250 |
| Lactose | 150 |

The 10-deazaaminopterin or 5,10- or 8,10-dideazaaminopterin compound and lactose are passed through a sieve and the powders well mixed together before filling into hard gelatin capsules of suitable size, so that each capsule contains 400 mg of mixed powders.

EXAMPLE 4

| Suppositories | Mg/suppositories |
| --- | --- |
| 10-deazaaminopterin or 5,10- or 8,10-dideazaaminopterin compound | 50 |

-continued

EXAMPLE 4

| Suppositories | Mg/suppositories |
| --- | --- |
| Oil of Theobroma | 950 |

The 10-deazaaminopterin or 5,10- or 8,10-dideazaaminopterin compound is powdered and passed through a sieve and triturated with molten oil of theobroma at 45° C. to form a smooth suspension.

The mixture is well stirred and poured into molds, each of nominal 1 g capacity, to product suppositories.

EXAMPLE 5

| Cachets | Mg/cachet |
| --- | --- |
| 10-deazaaminopterin or 5,10- or 8,10-dideazaaminopterin compound | 100 |
| Lactose | 400 |

The 10-deazaaminopterin or 5,10- or 8,10-dideazaaminopterin compound is passed through a mesh sieve, mixed with lactose previously sieved and fitted into cachets of suitable size so that each contains 500 mg.

EXAMPLE 6

| Intramuscular injection (sterile suspension in aqueous vehicle) | Mg |
| --- | --- |
| 10-deazaaminopterin or 5,10- or 8,10-dideazaaminopterin compound | 10 |
| Sodium citrate | 5.7 |
| Sodium carboxymethylcellulose (low viscosity grade) | 2.0 |
| Methyl para-hydroxybenzoate | 1.5 |
| Propyl para-hydroxylbenzoate | 0.2 |
| Water for injection to 1.0 ml | |

EXAMPLE 7

| Intraperitoneal intravenous or subcutaneous injection (sterile solution in aqueous carrier system) | Mg |
| --- | --- |
| 10-deazaaminopterin or 5,10- or 8,10-dideazaaminopterin compound, hydrochloric acid addition salt | 15 |
| Sodium citrate | 5.7 |
| Sodium carboxymethylcellulose (low viscosity grade) | 2.0 |
| Methyl para-hydroxybenzoate | 1.5 |
| Propyl para-hydroxylbenzoate | 0.2 |
| Water for injection to 1.0 ml | |

Having regard to the foregoing disclosure, the following is claimed as inventive and patentable embodiments thereof:

1. A process for the preparation of pteroic monocarboxylic acids having the general formula:

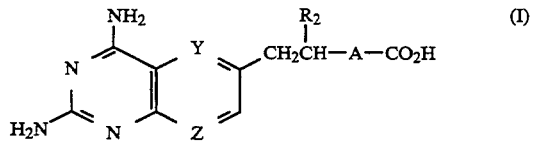

which comprises the steps:

(a) preparing a corresponding dicarboxylic acid ester from a corresponding dimethylhomoterephthalic acid dimethyl ester having the formula:

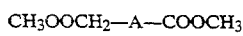

(b) coupling the corresponding dicarboxylic acid ester having the formula:

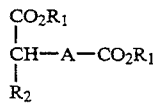

with the corresponding diazaaminopterin 6-methylene halide having the formula:

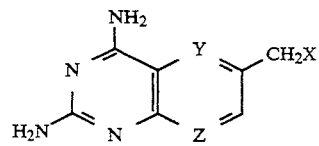

in the presence of an alkali metal alkaline compound selected from the group consisting of alkali metal hydrides, alkali metal alkoxides and alkali metal hydroxides, with the proviso that the alkali metal compound is not sodium halide or sodium cyanide, in solution of dimethyl sulfoxide at a reaction temperature at which the coupling proceeds but below decomposition temperature of coupling reaction product, thereby forming a pteroic acid diester having the formula:

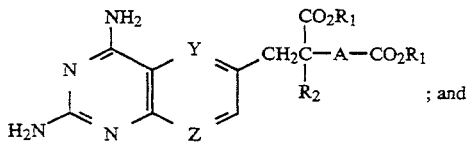
; and (c) hydrolysing the two ester groups to form the corresponding carboxylic acid groups, and then monodecarboxylating the diacid in the presence of an organic solvent at temperatures between 100° C. and 165° C. for about 5 to about 45 minutes, thereby removing the carboxylic acid group attached to the carbon alpha to the A group and forming a pteroic acid having the formula I, wherein X is halogen, such as chlorine, bromine or iodine;

Y is selected from the group consisting of N and $CR_3$, where $R_3$ is hydrogen, alkyl of from one to eight carbon atoms or chlorine;

Z is N or CH;

$R_1$ is selected from the group consisting of alkyl having from one to eight carbon atoms, cycloalkyl of from five to eight carbon atoms and aralkyl having from seven to eight carbon atoms;

$R_2$ is selected from the group consisting of alkyl having from one to eight carbon atoms, alkenyl and alkynyl having from three to eight carbon atoms; and A is selected from the group consisting of

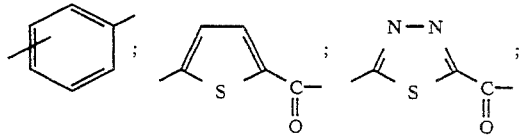

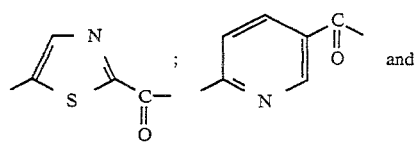

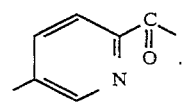

2. A process according to claim 1, in which the alkali metal alkaline compound is an alkali metal hydride.

3. A process according to claim 2, in the alkali metal hydride is sodium hydride.

4. A process according to claim 1, in which the diester of the pteroic acid is hydrolyzed in aqueous solution and then precipitated by addition of acid to a pH from about 4 to about 6.5.

5. A process according to claim 1, in which the monodecarboxylation is carried out by reacting the dicarboxylic acid in dry dimethylsulfoxide at a temperature within the range from about 135° to about 142° C. for about 10 minutes, followed by cooling the reaction mixture to temperatures within the range from about 30° to about 35° C.

6. The process according to claim 1 wherein the corresponding dicarboxylic acid ester is prepared by alkylation of the corresponding dimethylhomoterephthalic acid dimethyl ester.

7. In the process for the preparation of 10-deazaaminopterins and 5,10- and 8,10- dideazaaminopterins, the improvement which comprises the steps:

(a) preparing a corresponding dicarboxylic acid ester from a corresponding dimethylhomoterephthalic acid dimethyl ester having the general formula $CH_3OOCH_2—A—COOCH_3$ (b) coupling the corresponding dicarboxylic acid diester having the formula:

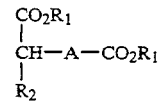
Ic with the corresponding diazaaminopterin 6-methylene halide having the formula:

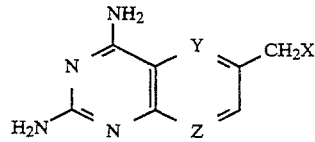
Ia in the presence of an alkali metal alkaline compound selected from the group consisting of alkali metal hydrides, alkali metal alkoxides and alkali metal hydroxides, provided that the alkali metal compound is not sodium halide or sodium cyanide in solution of dimethyl sulfoxide at a reaction temperature at which the coupling proceeds but below decomposition temperature of coupling reaction product, thereby forming a pteroic acid diester having the formula:

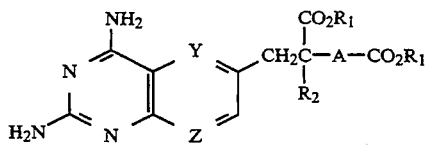

(c) hydrolysing the two diester groups to form the corresponding carboxylic acid groups, and then monodecarboxylating the diacid, in the presence of dry dimethylsulfoxide at temperatures between 100° and 165° C., thereby removing the carboxylic acid group attached to the carbon alpha to the A group and forming a pteroic acid having the formula:

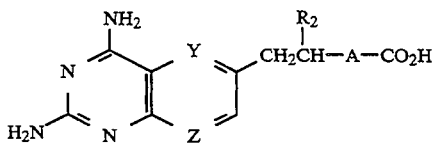

wherein

X is halogen

Y is selected from the group consisting of N and $CR_3$, where $R_3$ is hydrogen, alkyl of from one to eight carbon atoms or chlorine;

Z is N or CH;

$R_1$ is selected from the group consisting of alkyl having from one to eight carbon atoms, and cycloalkyl having from five to eight carbon atoms and aralkyl having from seven to eight carbon atoms phenyl, thiophene and phenethyl;

$R_2$ is selected from the group consisting of alkyl having from one to eight carbon atoms, alkenyl or alkynyl having from three to eight carbon atoms, or phenyl, thiophene and phenethyl; and A is selected from the group consisting of

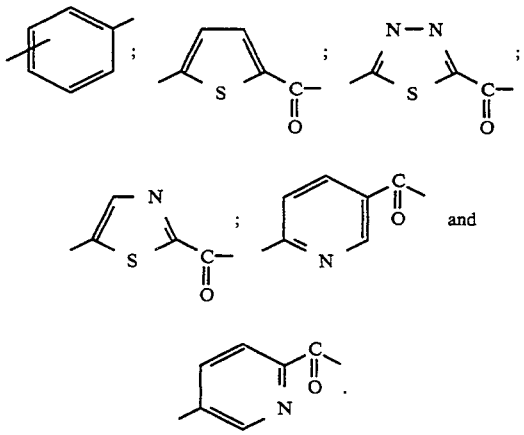

8. A process according to claim 7, in which the alkali metal alkaline compound is an alkali metal hydride.

9. A process according claim 8, in the alkali metal hydride is sodium hydride.

10. A process according to claim 7, in which the diester of the pteroic acid is hydrolyzed in aqueous solution and then precipitated by addition of acid to a pH from about 4 to about 6.5.

11. A process according to claim 7, in which the monodecarboxylation is carried out by reacting the dicarboxylic acid at a temperature within the range from about 135° to about 142° C. for about 10 minutes, followed by cooling the reaction mixture to temperatures within the range from about 30° to about 35° C.

12. The process according to claim 7 wherein the corresponding dicarboxylic acid ester is prepared by alkylation of the corresponding dimethylhomoterephthalic acid dimethyl ester.

* * * * *

Disclaimer 5,374,726—Joseph I. DeGraw, 880 Hanover Ave., Sunnyvale, Calif. 94087; William T. Colwell, 1055 Del Norte, Menlo Park, Calif. 94025; James R. Piper, 3128 Dolly Ridge Dr., Birmingham, Ala. 35243. PROCESS FOR PREPARING 10-DEAZAAMINOPTERINS AND 5,10- AND 8,10-DIDEAZAAMINOPTERINS FROM PTEROIC DICARBOXYLIC ACID DIESTERS. Patent dated Dec. 20, 1994. Disclaimer filed Jun 13, 2003, by the inventors.

Hereby enters this disclaimer to claims 1-12, of said patent.

*(Official Gazette, October 7, 2003)*